(12) United States Patent
Cedro et al.

(10) Patent No.: US 7,481,778 B2
(45) Date of Patent: Jan. 27, 2009

(54) GUIDEWIRE WITH DEFLECTABLE TIP HAVING IMPROVED FLEXIBILITY

(75) Inventors: Rudolph Cedro, Clinton, NJ (US); David D. Grewe, Glen Gardner, NJ (US); Hikmat Hojeibane, Princeton, NJ (US)

(73) Assignee: Cordis Corporation, Miami Lakes, FL (US)

(*) Notice: Subject to any disclaimer, the term of this patent is extended or adjusted under 35 U.S.C. 154(b) by 105 days.

(21) Appl. No.: 11/590,625

(22) Filed: Oct. 31, 2006

(65) Prior Publication Data

US 2007/0219465 A1   Sep. 20, 2007

Related U.S. Application Data

(63) Continuation-in-part of application No. 10/691,823, filed on Oct. 23, 2003, which is a continuation-in-part of application No. 10/224,168, filed on Aug. 20, 2002, now Pat. No. 7,128,718.

(60) Provisional application No. 60/366,739, filed on Mar. 22, 2002.

(51) Int. Cl.
  A61M 5/00    (2006.01)
  A61M 29/00   (2006.01)
  A61M 5/178   (2006.01)
  A61M 25/00   (2006.01)
  A61B 5/00    (2006.01)

(52) U.S. Cl. .............. 600/585; 604/96.01; 604/97.01; 604/98.01; 604/99.01; 604/104; 604/164.03; 604/164.13; 604/528

(58) Field of Classification Search ............... 600/585; 604/96.01, 97.01, 98.01, 99.01, 104, 164.03, 604/164.13, 528

See application file for complete search history.

(56) References Cited

U.S. PATENT DOCUMENTS

| | | | | |
|---|---|---|---|---|
| 4,003,369 A | * | 1/1977 | Heilman et al. | 600/585 |
| 4,183,434 A | * | 1/1980 | Watt | 206/438 |
| 4,665,906 A | * | 5/1987 | Jervis | 606/78 |
| 4,719,924 A | * | 1/1988 | Crittenden et al. | 600/585 |
| 4,757,827 A | * | 7/1988 | Buchbinder et al. | 600/585 |
| 4,770,188 A | * | 9/1988 | Chikama | 600/585 |
| 4,813,434 A | * | 3/1989 | Buchbinder et al. | 600/585 |
| 4,815,478 A | * | 3/1989 | Buchbinder et al. | 600/585 |
| 4,827,841 A | * | 5/1989 | White, Sr. | 101/66 |
| 4,827,941 A | * | 5/1989 | Taylor et al. | 600/434 |
| 4,854,325 A | * | 8/1989 | Stevens | 600/434 |
| 4,875,489 A | * | 10/1989 | Messner et al. | 600/585 |
| 4,881,981 A | * | 11/1989 | Thoma et al. | 148/563 |
| 4,886,067 A | * | 12/1989 | Palermo | 600/434 |
| 4,921,482 A | * | 5/1990 | Hammerslag et al. | 604/95.01 |
| 4,923,462 A | * | 5/1990 | Stevens | 606/159 |

(Continued)

*Primary Examiner*—Max Hindenburg
*Assistant Examiner*—Jeffrey G Hoekstra
(74) *Attorney, Agent, or Firm*—Michael W. Montgomery

(57) ABSTRACT

A steerable guidewire having a deflectable distal tip which comprises a longitudinal hypotube and an interlocking spring coil attached to the distal end of the hypotube and also includes a longitudinally movable deflection member which is attached to the distal end of the spring coil and a tip retaining ribbon which extends from the distal end of the hypotube to the distal end of the spring coil for providing very precise deflection of the distal tip. The distal end of the deflection member has "skived," or tapered, sides to enhance the flexibility of the guidewire.

6 Claims, 6 Drawing Sheets

U.S. PATENT DOCUMENTS

| | | | | |
|---|---|---|---|---|
| 4,925,445 A * | 5/1990 | Sakamoto et al. | ............ | 604/528 |
| 4,935,068 A * | 6/1990 | Duerig | ........................ | 148/563 |
| 4,935,088 A * | 6/1990 | Mitsuyama | .............. | 156/272.4 |
| 4,936,845 A * | 6/1990 | Stevens | ........................ | 606/159 |
| 4,940,062 A * | 7/1990 | Hampton et al. | ............ | 600/585 |
| 4,953,553 A * | 9/1990 | Tremulis | .................... | 600/486 |
| 4,966,163 A * | 10/1990 | Kraus et al. | .................. | 600/585 |
| 4,984,581 A * | 1/1991 | Stice | ............................ | 600/585 |
| 4,998,916 A * | 3/1991 | Hammerslag et al. | ........ | 604/528 |
| 5,037,391 A * | 8/1991 | Hammerslag et al. | ........ | 604/528 |
| 5,060,660 A * | 10/1991 | Gambale et al. | ............ | 600/585 |
| 5,069,226 A * | 12/1991 | Yamauchi et al. | ........... | 600/585 |
| 5,078,722 A * | 1/1992 | Stevens | ........................ | 606/159 |
| 5,116,350 A * | 5/1992 | Stevens | ........................ | 606/159 |
| 5,120,308 A * | 6/1992 | Hess | ........................ | 604/170.01 |
| 5,125,395 A * | 6/1992 | Adair | .......................... | 600/121 |
| 5,133,364 A * | 7/1992 | Palermo et al. | .............. | 600/585 |
| 5,143,085 A * | 9/1992 | Wilson | ........................ | 600/585 |
| 5,159,937 A * | 11/1992 | Tremulis | .................... | 600/585 |
| 5,188,621 A * | 2/1993 | Samson | ........................ | 604/528 |
| 5,190,050 A * | 3/1993 | Nitzsche | ...................... | 600/585 |
| 5,203,772 A * | 4/1993 | Hammerslag et al. | ........ | 604/528 |
| 5,242,394 A * | 9/1993 | Tremulis | ................. | 604/96.01 |
| 5,341,818 A * | 8/1994 | Abrams et al. | .............. | 600/585 |
| 5,365,942 A * | 11/1994 | Shank | ......................... | 600/585 |
| 5,368,049 A * | 11/1994 | Raman et al. | ................ | 600/585 |
| 5,372,587 A * | 12/1994 | Hammerslag et al. | .... | 604/95.04 |
| 5,397,305 A * | 3/1995 | Kawula et al. | ........... | 604/96.01 |
| 5,480,382 A * | 1/1996 | Hammerslag et al. | ........ | 604/528 |
| 5,501,694 A * | 3/1996 | Ressemann et al. | .......... | 606/159 |
| 5,695,111 A * | 12/1997 | Nanis et al. | .................. | 228/206 |
| 5,807,279 A * | 9/1998 | Viera | .......................... | 600/585 |
| 5,813,997 A * | 9/1998 | Imran et al. | .................. | 600/585 |
| 5,882,333 A * | 3/1999 | Schaer et al. | ............. | 604/95.01 |
| 5,891,055 A * | 4/1999 | Sauter | ......................... | 600/585 |
| 5,908,405 A * | 6/1999 | Imran et al. | .................. | 604/508 |
| 5,931,830 A * | 8/1999 | Jacobsen et al. | ............. | 604/523 |
| 6,027,460 A * | 2/2000 | Shturman | ..................... | 600/585 |
| 6,059,739 A * | 5/2000 | Baumann | ..................... | 600/585 |
| 6,126,649 A * | 10/2000 | VanTassel et al. | ........... | 604/528 |
| 6,146,338 A * | 11/2000 | Gardeski et al. | ............. | 600/585 |
| 6,193,706 B1 * | 2/2001 | Thorud et al. | ................ | 604/533 |
| 6,273,876 B1 * | 8/2001 | Klima et al. | ................. | 604/264 |
| 6,306,105 B1 * | 10/2001 | Rooney et al. | .............. | 600/585 |
| 6,352,515 B1 * | 3/2002 | Anderson et al. | ............ | 600/585 |
| 6,355,016 B1 * | 3/2002 | Bagaoisan et al. | ..... | 604/103.09 |
| 6,375,628 B1 * | 4/2002 | Zadno-Azizi et al. | ........ | 600/585 |
| 6,379,369 B1 * | 4/2002 | Abrams et al. | .............. | 606/159 |
| 6,468,230 B2 * | 10/2002 | Muni et al. | .................. | 600/585 |
| 6,488,637 B1 * | 12/2002 | Eder et al. | ................... | 600/585 |
| 2002/0019599 A1 * | 2/2002 | Rooney et al. | .............. | 600/585 |
| 2002/0038129 A1 * | 3/2002 | Peters et al. | ................ | 606/167 |
| 2002/0049392 A1 * | 4/2002 | DeMello | ...................... | 600/585 |
| 2002/0151966 A1 * | 10/2002 | Eder et al. | ................. | 623/1.18 |
| 2002/0165534 A1 * | 11/2002 | Hayzelden et al. | ............ | 606/41 |
| 2003/0105415 A1 * | 6/2003 | Mirigian | ..................... | 600/585 |

\* cited by examiner

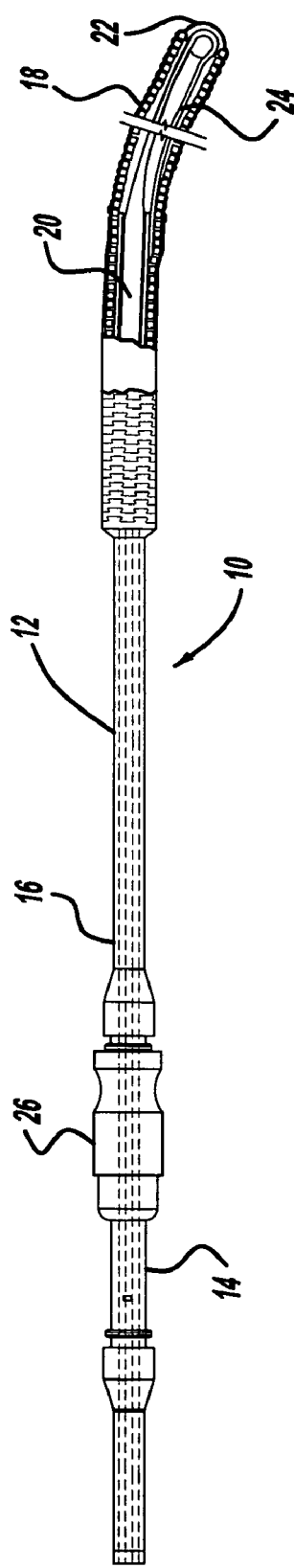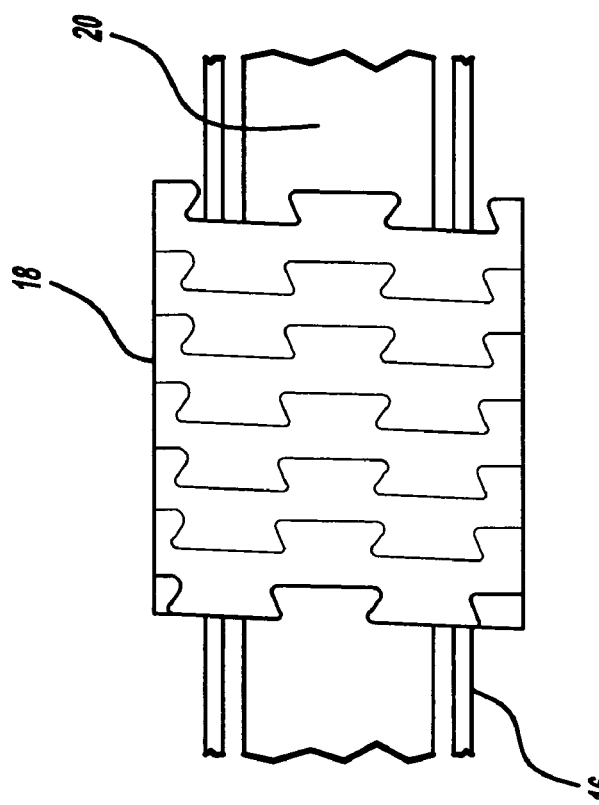

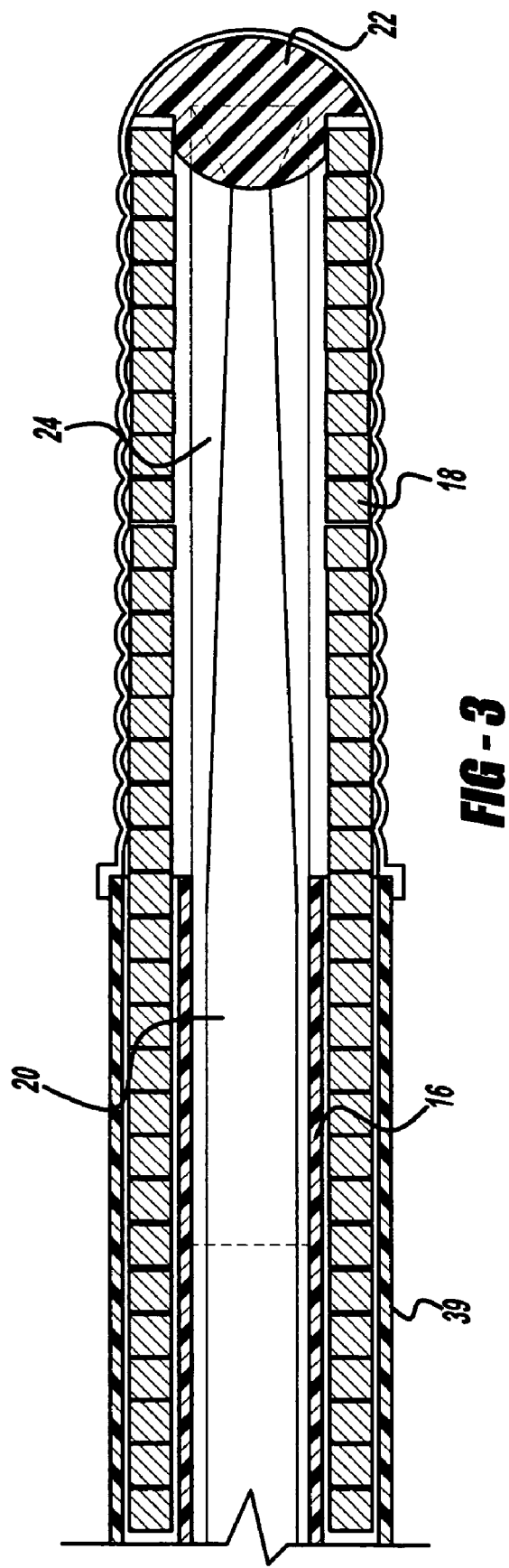

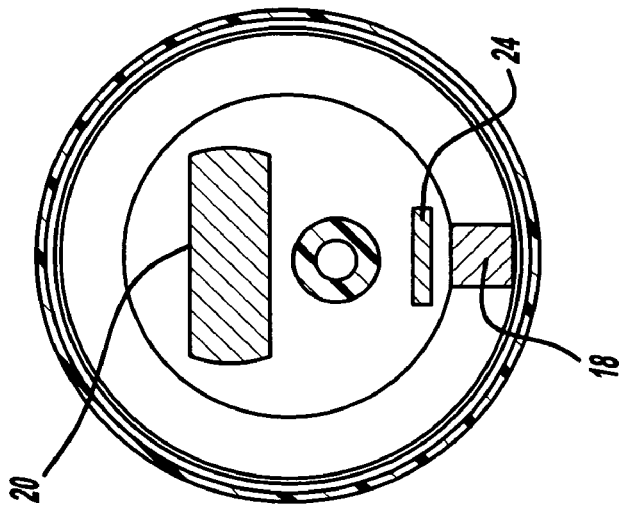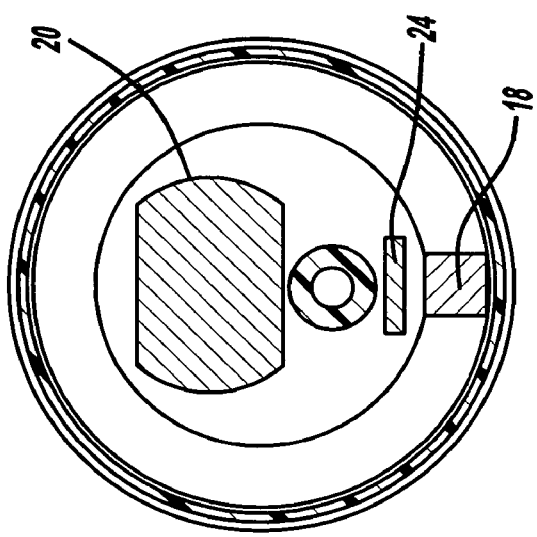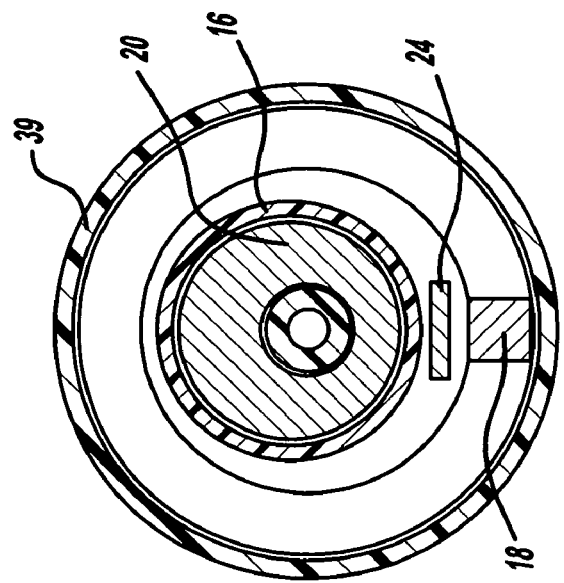

GUIDEWIRE WITH DEFLECTABLE TIP HAVING IMPROVED FLEXIBILITY

CROSS-REFERENCE TO RELATED APPLICATIONS(S)

This patent application is a continuation-in-part of U.S. patent application Ser. No. 10/691,823, filed on Oct. 23, 2003, entitled, "Guidewire With Deflectable Tip Having Improved Torque Characteristics," which is a continuation-in-part of U.S. patent application Ser. No. 10/224,168, filed on Aug. 20, 2002, entitled, "Guidewire With Deflectable Tip," now issued as U.S. Pat. No. 7,128,718, which is a nonprovisional patent application of U.S. patent application Ser. No. 60/366,739, filed on Mar. 22, 2002, entitled, "Deflection Wire Concept."

BACKGROUND OF THE INVENTION

1. Field of the Invention

The present invention relates to a steerable guidewire and more particularly to a steerable guidewire having a tip which may be very precisely steered or deflected. The guidewire is particularly suitable for use in conjunction with the insertion of a catheter into a vessel of the body, or alternatively, the guidewire may be used to open obstructions within a vessel.

2. Description of the Prior Art

For many years guidewires have included a core wire with the distal end being tapered and with a coil spring mounted on the tapered distal end. These guidewires have been used to facilitate the insertion of a catheter into a vessel of the body. Generally, the guidewire is inserted into a vessel, a catheter is inserted over the guidewire and the catheter is then moved through the vessel until the distal end of the catheter is positioned at a desired location. The guidewire is then retracted from the catheter and the catheter is left in the vessel. Alternatively, the guidewire may be first inserted into the catheter with the distal portion of the guidewire extending beyond the distal end of the catheter. This assembly is then inserted into a vessel with the distal tip of the guidewire being used to facilitate movement of the guidewire and catheter through the vessel. Again, when the distal tip of the catheter has been placed in a desired location, the guidewire may be retracted thereby leaving the catheter in place within the vessel.

Another common application for guidewires is that of using the distal tip of the guidewire for removing an obstruction within a vessel. Often times this procedure is accomplished by inserting the guidewire within a vessel, moving the distal tip of the guidewire into contact with the obstruction and then very gently tapping the distal tip of the guidewire against the obstruction until the guidewire passes through the obstruction. Alternatively, various types of devices may be placed on the distal end of a guidewire for actively opening an obstruction within the vessel. Examples of such devices which may be placed on the end of the guidewires in order to open an obstruction are disclosed in the following United States patents to Robert C. Stevens: U.S. Pat. Nos. 5,116,350; 5,078,722; 4,936,845; 4,923,462; and 4,854,325.

While most guidewires used today do not include a mechanism for deflecting or steering the tip of the guidewire, it is very desirable to provide tip steering in order to facilitate movement of the guidewire through the tortuous vessels of the body. There are many patents directed toward different mechanisms for deflecting the distal tip of a guidewire in order to steer the guidewire. Examples of such guidewires are disclosed in the following patents: U.S. Pat. No. 4,815,478 to Maurice Buchbinder, et al., U.S. Pat. No. 4,813,434 to Maurice Buchbinder, et al., U.S. Pat. No. 5,037,391 to Julius G. Hammerslag, et al., U.S. Pat. No. 5,203,772 to Gary R. Hammerslag, et al., U.S. Pat. No. 6,146,338 to Kenneth C. Gardeski, et al., U.S. Pat. No. 6,126,649 to Robert A. VanTassel, et al., U.S. Pat. No. 6,059,739 to James C. Baumann and U.S. Pat. No. 5,372,587 to Julius G. Hammerslag, et al. U.S. Pat. No. 4,940,062 to Hilary J. Hampton, et al., discloses a balloon catheter having a steerable tip section. All of the above-identified patents are incorporated herein by reference.

While each of the latter group of patents disclose guidewires having some degree of steerability, there is a need to have a guidewire with very precise steering in a guidewire of a very small diameter which is suitable for the purposes described above. More particularly, there is an important need for a very small diameter guidewire having improved torque characteristics which includes a distal tip which may be deflected very precisely in either of two directions to enhance steerability.

SUMMARY OF THE INVENTION

In accordance with one aspect of the present invention, there is provided a very small diameter steerable guidewire having a deflectable tip which includes an elongated flexible tubing, a flexible helical coil attached to the distal portion of the flexible tubing, an elongated deflection member which is slidably disposed within the tubing and within the helical coil. The deflection member is of a cylindrical configuration and the distal portion has a flattened side which tapers from a position proximal to the distal end of the deflection member to a position at about the distal end of the deflection member. Preferably, the distal portion also has a second flattened side on the opposite side of the deflection member which also tapers from a position proximal to the distal end to a position at about the distal end. More preferably, the one flattened side or both flattened sides of the distal portion taper substantially uniformally over the length of the tapered portion(s). In addition, a retaining ribbon is attached to the distal end of the flexible tubing and is oriented to extend in a plane which is generally parallel to the plane of the flattened side of the deflection member. An attachment member which may take the form of a rounded bead, preferably formed from epoxy, is bonded to the distal end of the helical coil, the distal end of the deflection member and the distal end of the retaining ribbon so that longitudinal movement of the deflection member causes the distal end of the helical coil to be deflected. With the flattened side or sides of the distal tip of the deflection member, the guidewire can be easily deflected in opposite directions but in a single plane, i.e., there is substantially no twisting of the guidewire upon deflection.

In accordance with another aspect of the present invention, the distal tip of the deflection member is preferably pre-shaped into a curved configuration to thereby cause the flexible helical coil to be biased into a normally curved shape.

In accordance with a further aspect of the present invention, the distal portion of the deflection member engages the attachment member, or rounded bead, at a location offset from the center of the attachment member, and the distal portion of the retaining ribbon engages the attachment member at a location offset from the center of the attachment member. Preferably, the retaining ribbon engages the attachment member at a location offset from the center portion of the attachment member in the opposite direction from the offset location of the deflection member.

In accordance with still another aspect of the present invention, the distal tip of the deflection member and the retaining ribbon are connected to each other within the attachment member. Preferably these two elements are formed as a single unitary element. In a preferred embodiment of the invention the deflection member is further flattened at its distal end to form the retaining ribbon. The retaining ribbon is bent 180 degrees with respect to the deflection member to form a generally U-shaped bend to thereby establish a predetermined spacing between the deflection member and the retaining ribbon and to also cause these members to remain parallel to each other.

BRIEF DESCRIPTION OF THE DRAWINGS

FIG. 1 is an enlarged elevational view of a balloon on a guidewire having a deflectable tip and control handle in accordance with the one aspect of the present invention;

FIG. 2A is an expanded elevational view of the interlocking coil portion of the guidewire shown in FIG. 1;

FIG. 3 is an enlarged sectional view showing the distal end of the steerable guidewire of FIG. 2 rotated 90 degrees;

FIGS. 3A, 3B and 3C are all section views taken along lines 3A-3A, 3B-3B and 3C-3C of FIG. 2 which illustrate the cross-sectional configuration of the distal section of the guidewire taken at three different locations; and, FIGS. 4 and 5 are sectional views showing the steerable guidewire deflected from its normal position to opposite extremes of deflection.

DESCRIPTION OF THE PREFERRED EMBODIMENT

Figure 2:
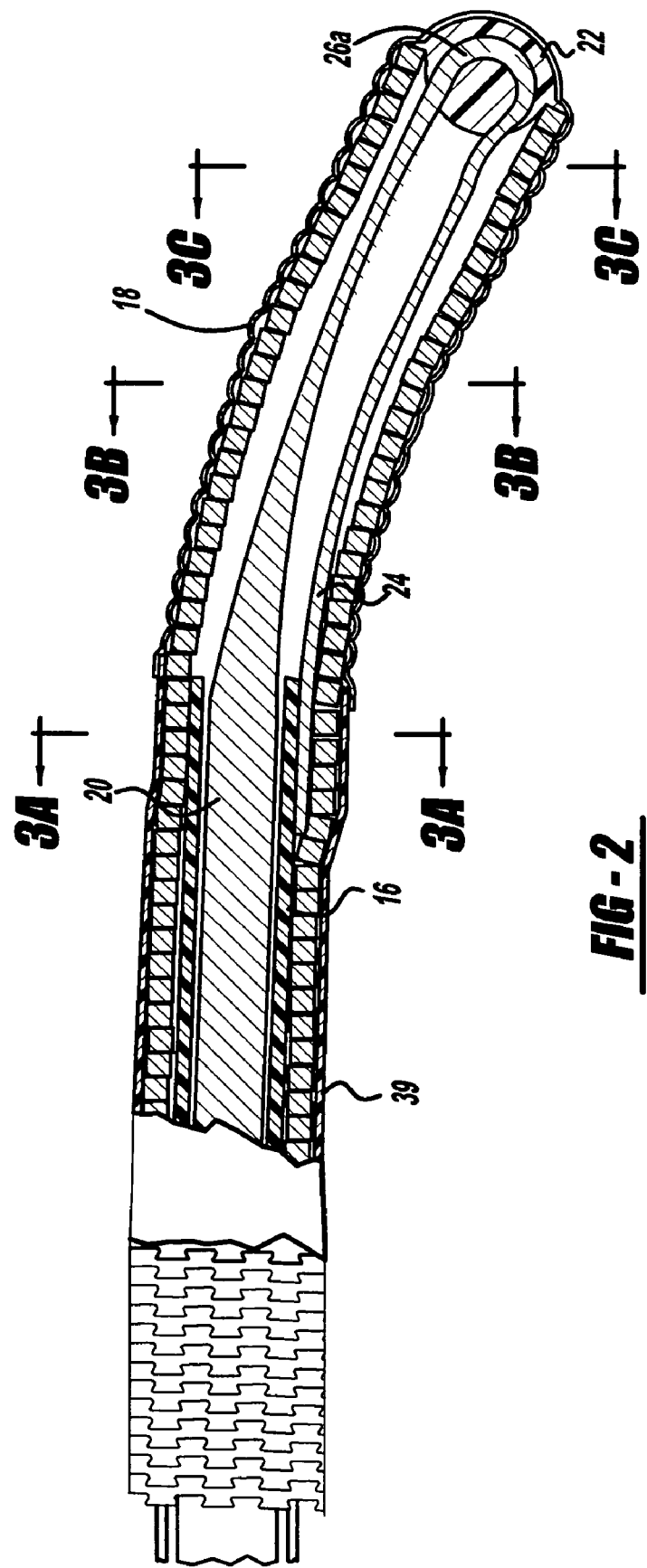
FIG. 2 is an enlarged sectional side view showing the guidewire in its normal pre-shaped position.

FIG. 1 generally illustrates a steerable guidewire system 10 which embodies the present invention and comprises a steerable guidewire 12 coupled to a control handle 14. More particularly, the steerable guidewire comprises an elongated hypotube 16, a helical coil 18 attached to and extending from the distal end of the hypotube 16. The helical coil 18 is of a rectangular or square cross-sectional configuration and is preferably formed from platinum tungsten with the proximal turns being wound such that adjacent turns of the proximal portion are in contact, or loosely interlocked with each other.

While the preferred embodiment of the present invention includes the helical coil 18, this element may take the form of any flexible rectangular or square cross-sectional member, such as for example a thin square metallic tube with or without portions of the tube removed, for example laser cutting, so as to form a very flexible cylindrical or square member. An elongated deflection member 20 extends from the proximal end of the control handle through the hypotube 16 and through the helical coil 18, and is connected into an attachment member, or rounded bead 22, which is disposed at the distal tip of the helical coil 18. In addition, a retaining ribbon 24 is connected to the distal end of the hypotube 16 and is also connected to the rounded bead 22.

The control handle 14 generally comprises a slidable control knob 26 which may be moved longitudinally with respect to the control handle. The control handle 14 is coupled to the deflection member 20. As will be discussed in more detail, the longitudinal movement of the slidable control knob 26 causes deflection of the distal tip of the guidewire in either an upward or downward direction.

FIGS. 2 and 3 illustrate in more detail the distal portion of the steerable guidewire 12. FIG. 3 is a view of the guidewire 12 shown in FIG. 2 with the guidewire being rotated 90 degrees about its longitudinal axis. More particularly, and with reference to FIGS. 2 and 3, the proximal end of the helical coil 18 is bonded, preferably by use of an epoxy, to the outer surface near the distal end of the hypotube 16. The elongated deflection member 20 takes the form of a small diameter cylindrical wire having an intermediate portion in which both sides of the cylindrical deflection member are skived, or tapered, to form flat sides on both the top and the bottom of the cylindrical deflection member. The flattened sides are preferably tapered uniformly over the entire intermediate portion to a point where the intermediate section contacts the rounded bead 22. The most distal end of the cylindrical wire 20 is further flattened to a thickness of approximately 0.0015 inches and is bent back 180 degrees to form a deflection member 20 having a U-shaped bend 26a between the deflection member 20 and the retaining ribbon 24. The proximal end of the retaining ribbon 24 is bonded, preferably by use of epoxy, to the outer surface of the distal end of the hypotube 16. The retaining ribbon 24 is aligned in a plane parallel to the plane of the flattened deflection member 20 and the U-shaped portion is encapsulated by the bead 22, which preferably takes the form of a rounded epoxy bead which is bonded to the distal tip of the helical coil 18.

As may be appreciated, with this unitary construction of the deflection member 20 and the retaining ribbon 24, these members remain aligned so that both lie in planes parallel to each other. In addition, the U-shaped bend portion when encapsulated into the bead 22 causes the retaining ribbon 24 and deflection member 20 to be properly spaced with respect to each other.

As further illustrated in FIG. 2, the retaining ribbon 24 is preferably attached to the bead 22 at a position offset from the center of the bead in the same direction that the retaining ribbon 24 is offset from the longitudinal axis of the steerable guidewire 12. In addition, the deflection member 20 is attached to the bead 22 at a position offset from the center of the bead in an opposite direction from the offset of the retaining ribbon 24.

Also, as may be seen in FIG. 2, the deflection member 20 and the retaining ribbon 24 are pre-shaped into an arcuate, or curved, configuration to thereby maintain the helical coil 18 in a normally curved configuration. The retaining ribbon 24 and the deflection member 20 are pre-shaped such that the distal tip of the guidewire curves away from the longitudinal axis of the guidewire in a direction toward that side of the guidewire containing the retaining ribbon 24.

As illustrated in FIG. 2A, the helical coil 18 is formed as an elongated member having a rectangular, or square, cross-sectional configuration and wound in a helical configuration. In addition, the helical coil 18 is formed with re-occurring steps, or step undulation, which when wound into a helical configuration so that adjacent turns to loosely interlock thereby preventing movement between adjacent turns. Such interlocking turns enhance the rotational rigidity or "torque-ability" of the coil such that when the proximal end of the coil is rotated 180 degrees, the distal end of the coil will rotate approximately 180 degrees. Accordingly, the distal end of the coil more nearly tracks, rotationally, the proximal end of the coil thereby significantly improving the "torsional" characteristics of the coil. By improving the "torsional" chacteristics of the coil, the overall characteristics of to guidewire are significantly improved.

As opposed to winding an elongated member to form the helical coil 18, a preferred method of forming the helical coil is by laser cutting the coil from a single thin-walled tube of an alloy in the undulations locking, stepped configuration as illustrated in FIG. 2A. Such laser cutting provides a coil with precise mating surfaces to assure proper interlocking between adjacent turns of the helical coil.

FIGS. 3A, 3B and 3C are sectional views of the deflection member 20 taken along lines 3A-3A, 3B-3B and 3C-3C of FIG. 2 and illustrate the configuration of the distal section of the deflection member 20 taken at three different locations. More particularly, FIG. 3A illustrates the cylindrical cross-sectional configuration of the proximal body portion of the deflection member 20. FIGS. 3B and 3C illustrate the distal portion of the deflection member 20 with "skived," or tapered, sides on both the top and bottom sides of the distal portion and also illustrate, taken along with FIG. 2, the preferred uniform tapering of the top and bottom sides of the distal portion of the deflection member 20 from the location where the tapering begins to about the distal end of the intermediate portion.

With the flattened top and bottom side of the distal tip, the distal section of the guidewire exhibits the characteristic of being very flexible in both directions of deflection, but more rigid to bending outside of the plane of preferred deflection. Accordingly, this construction provides improved flexibility to bending in a bi-directional manner, but resists twisting or bending outside the plane of preferred deflection.

Figure 4:
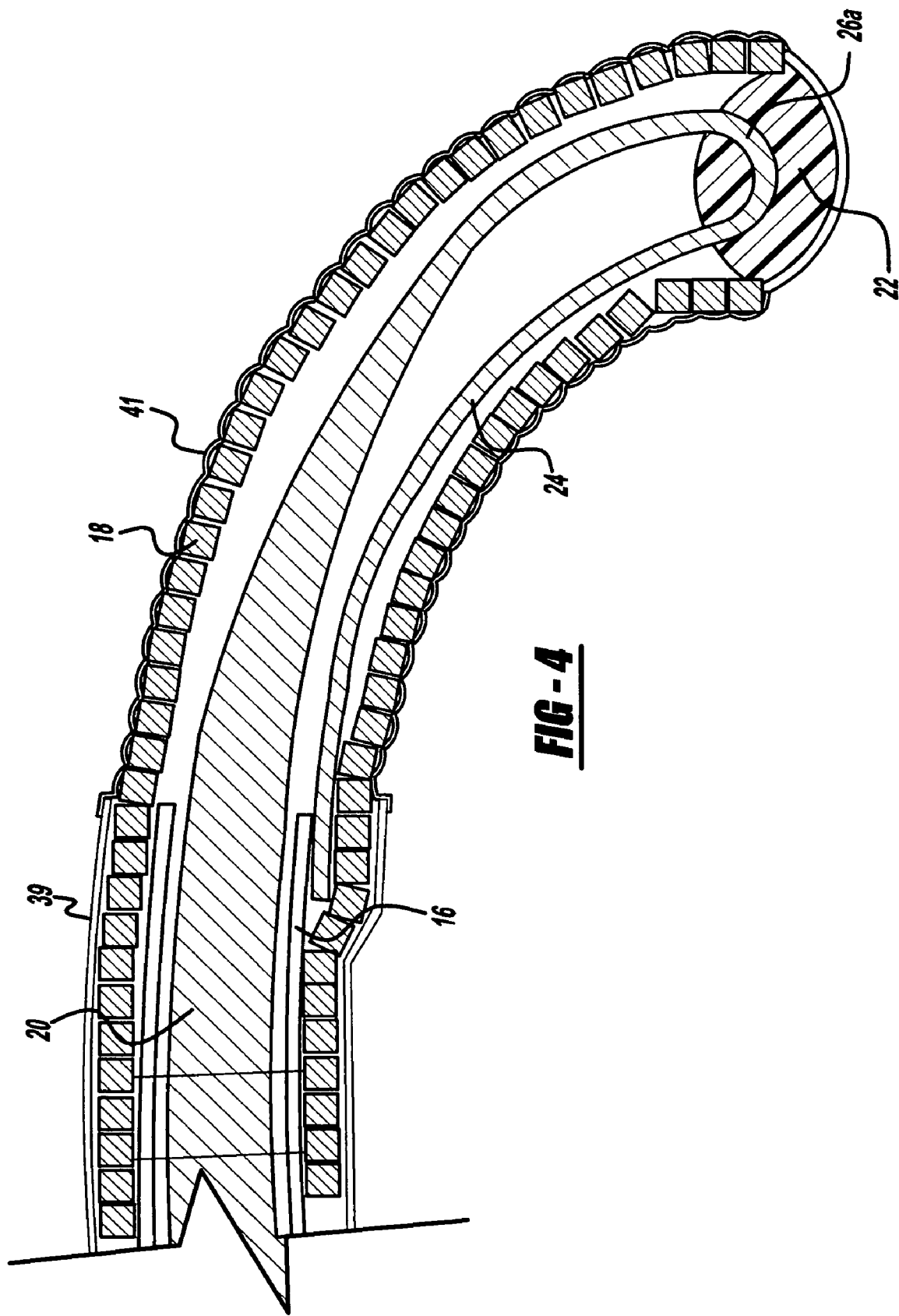

In operation, as previously described, the distal tip of the steerable guidewire 12 is normally biased into a downwardly curved position as illustrated in FIG. 2 because of the curve of the pre-shaped deflection member 20 and the retaining ribbon 24. When the slidable control knob 26 is moved distally as shown in FIG. 4, the deflection member 20 will be moved distally. As the deflection member 20 is moved distally, a pushing force is applied to the top portion of the rounded bead 22. The retaining ribbon 24 is attached to the lower portion of the bead 22 to thereby maintain the bead at a fixed distance from the distal end of the hypotube 16. As the deflection member 20 is moved to the right, the tip of the guidewire is caused to deflect downwardly to a maximum deflected position.

Since the deflection member 20 and the retaining ribbon 24 are pre-shaped prior to any activation of the steerable guidewire, the amount of force required to deflect the guidewire in this direction by moving the deflection member 20 is very small thereby preventing buckling of the deflection member. As the deflection member 20 is moved distally, the upper turns of the helical coil become slightly stretched and the lower turns of the coil become slightly compressed. The retaining ribbon 24 has a thickness of about 0.002 inches to thereby provide sufficient stiffness to prevent the buckling of these elements when the deflection member 20 is pushed distally. This construction also provides sufficient stiffness to transmit the necessary force from the proximal end to the distal end of the guidewire.

Figure 5:
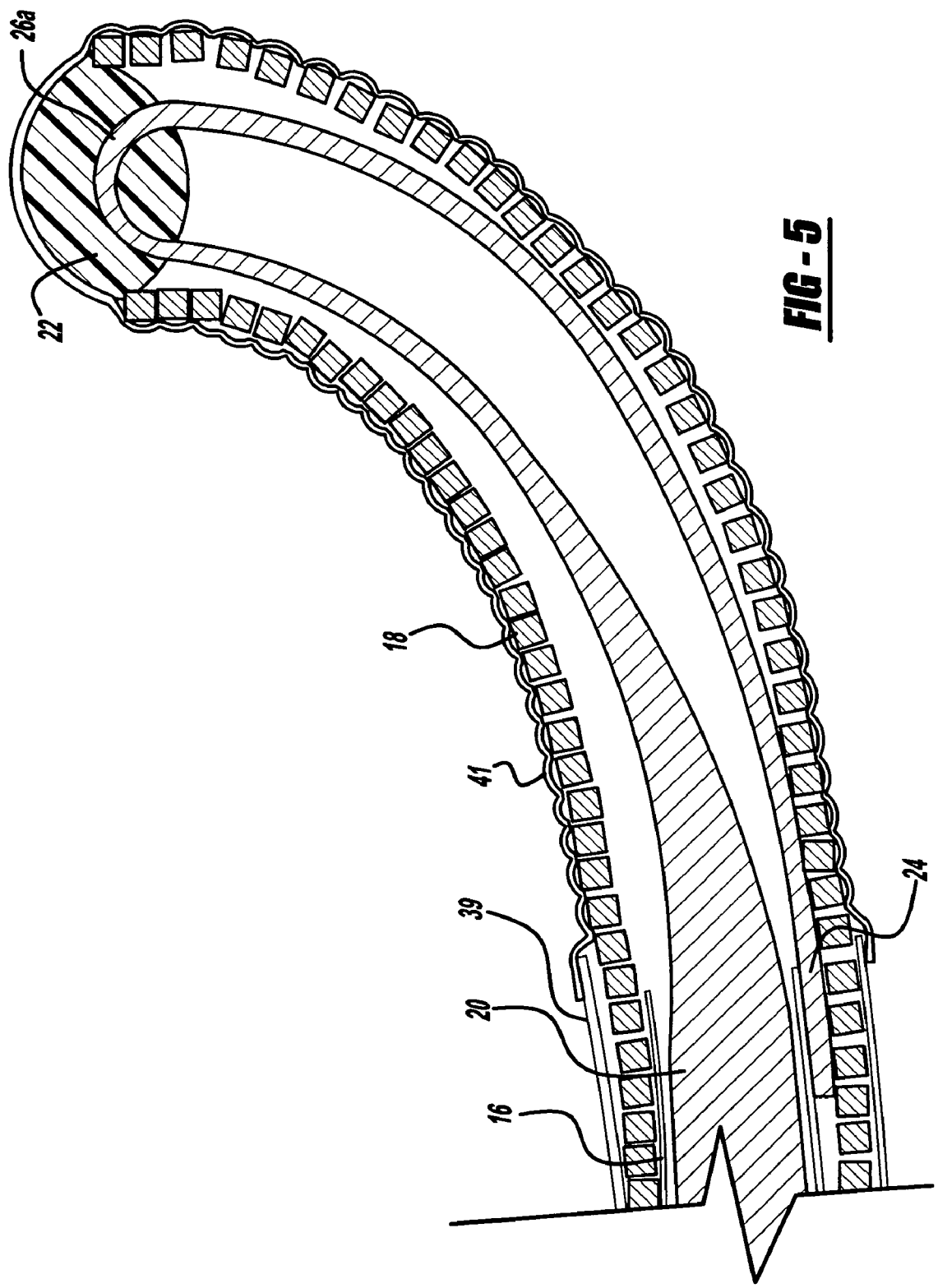

When the slidable control knob 26 is moved in a proximal direction as shown in FIG. 5, the deflection member 20 will be moved to the left to thereby cause the deflection member to pull on the top portion of the bead 22. Since again the retaining ribbon 24 causes the lower portion of the bead to remain at a fixed distance from the distal end of the hypotube 16, the tip of the guidewire 12 is caused to bend in an upward direction to a maximum deflection as shown in FIG. 5. Since the deflection member 20 is in tension when the slidable control knob is moved in a proximal direction, there is no concern for buckling of the deflection member. As the deflection member 20 is moved proximally, the upper coil turns become slightly compressed and the lower coil turns become somewhat stretched.

As previously discussed, when the proximal end of the guidewire 12 is rotated by a physician to "steer" the distal end of the guidewire, with the interlocking turns of adjacent coils of the helical coil 18, the distal tip will rotate on a one-to-one basis with respect to the proximal end of the hypotube 16. In other words, there is no "play" or "lag" between rotation of the proximal end and the distal end of the guidewire.

In a preferred embodiment of the present invention, the elongated deflection member 20 and the retaining ribbon 24 are constructed of nitinol, but these elements may be formed from other flexible materials including polymers. The helical coil 18 preferably formed by laser cutting as previously discussed, is constructed from an alloy comprised of about 92 percent platinum and 8 percent tungsten, but this element may also be constructed from numerous other materials. It is desirable that the coil exhibit the characteristic of being radiopaque to X-rays to assist in the positioning of the distal tip of the steerable guidewire 12. The deflection member 20 is formed from a single cylindrical nitinol wire of about 0.0065 inches in diameter having an intermediate portion which is flattened to form the deflection member 20 with a tapered thickness of about 0.002 inches, and a distal portion which is flattened to form the retaining ribbon 24 with a thickness of about 0.0015 inches. The retaining ribbon 24 is bent back 180 degrees to form a generally U-shaped bend, which is subsequently encapsulated within the rounded bead 22. The rounded bead 22 is preferably formed with epoxy, but may be formed with soldering or by welding.

It has been found that the addition of graphite between the deflection member 20 and the inner lumen of the hypotube 16 provides lubrication. Other lubricants, such as Teflon or MDX may be used for this purpose. The helical coil 18 is preferably coated with an elastomeric polymer 41 on its distal end to act as a sealant preventing the entry of blood and contrast media into the guidewire and a fluorinated polymer 39, such as Teflon, on its proximal end for lubrication purposes.

It may be seen that the guidewire as disclosed may be very easily and very precisely rotated and then deflected in either of two directions for very precise steering of the guidewire through the vessels of the body. As may be apparent, the disclosed guidewire may be used for placement of a catheter within the vasculature of the human body, it may be used by itself to cross an obstruction within the vessels or it may be used to carry a therapeutic device mounted on the distal end of the guidewire for purposes of removing obstructions which may exist within a vessel of the body.

The preceding specific embodiment is illustrated of the practice of this invention. It is to be understood, however, that other variations may also be employed without departing from the spirit and scope of the invention as hereinafter claimed.

That which is claimed is:

1. A steerable guidewire having a deflectable tip, said steerable guidewire comprising:

an elongated flexible tubing having proximal and distal portions;

a flexible helical coil having multiple turns and having proximal and distal ends the proximal end of said helical coil is attached to the distal portion of the flexible tubing;

a cylindrical elongated deflection member having a proximal portion and a distal end and being slidably disposed within said tubing and within said helical coil, the proximal portion of said cylindrical deflection member being generally cylindrical and having a first flattened side which tapers from an intermediate section to the distal end of the deflection member;

a retaining ribbon having proximal and distal ends, the proximal end of the retaining ribbon is attached to the distal portion of the flexible tubing and the retaining ribbon is oriented to extend in a plane which is generally parallel to the flattened side of the deflection member;

wherein the retaining ribbon and the deflection member are normally biased in an arcuate configuration to thereby cause the distal end of the helical coil to be normally biased in a curved shape; and, an attachment member engaging the distal end of the helical coil, the distal end of the deflection member and the distal end of the retaining ribbon so that longitudinal movement of the deflection member in a distal direction causes the distal end of the helical coil to be deflected in one direction and longitudinal movement of the deflection member in a proximal direction causes the distal end of the helical coil to deflect in another opposite direction; wherein the attachment member takes the form of a rounded bead which contacts the distal end of the helical coil to define a circular surface at the distal end of the coil and the distal end of the deflection member engages the rounded bead at a location radially offset from the center of the circular surface of the rounded bead.

2. A steerable guidewire as defined in claim 1, wherein said first flattened side of the deflection member tapers substantially uniformly from the intermediate section to the distal end of the deflection member.

3. A steerable guidewire as defined in claim 1, wherein the deflection member has a second side on the opposite side of the deflection member from that of the first flattened side which tapers from the intermediate section to the distal end of the deflection member.

4. A steerable guidewire as defined in claim 3, wherein said first and second sides of the deflection member taper substantially uniformly from the intermediate section to the distal end of the deflection member.

5. A steerable guidewire having a deflectable tip, said steerable guidewire comprising:

an elongated flexible tubing having proximal and distal portions;

a flexible helical coil having multiple turns and having proximal and distal ends, the proximal end of said helical coil is attached to the distal portion of the flexible tubing;

a cylindrical elongated deflection member having a proximal portion and a distal end and being slidably disposed within said tubing and within said helical coil, the proximal portion of said cylindrical deflection member being generally cylindrical and having a first flattened side which tapers from an intermediate section to the distal end of the deflection member;

a retaining ribbon having proximal and distal ends, the proximal end of the retaining ribbon is attached to the distal portion of the flexible tubing and the remaining ribbon is oriented to extend in a plane which is generally parallel to the flattened side of the deflection member; wherein the retaining ribbon and the deflection member are normally biased in an arcuate configuration to thereby cause the distal end of the helical coil to be normally biased in a curved shape; and an attachment member engaging the distal end of the helical coil, the distal end of the deflection member and the distal end of the retaining ribbon so that longitudinal movement of the deflection member in a distal direction causes the distal end of the helical coil to be deflected in one direction and longitudinal movement of the deflection member in a proximal direction causes the distal end of the helical coil to deflect in another opposite direction; wherein the attachment member takes the form of a rounded bead which contacts the distal end of the helical coil to define a circular surface at the distal end of the coil and the distal end of the deflection member engages the rounded bead at a location radially offset from the center of the circular surface of the rounded bead.

6. A steerable guidewire as defined in claim 5, wherein the rounded bead is formed from an epoxy material.

* * * * *

UNITED STATES PATENT AND TRADEMARK OFFICE
CERTIFICATE OF CORRECTION

PATENT NO. : 7,481,778 B2
APPLICATION NO. : 11/590625
DATED : January 27, 2009
INVENTOR(S) : Rudolph Cedro et al.

Page 1 of 1

It is certified that error appears in the above-identified patent and that said Letters Patent is hereby corrected as shown below:

Column 4 Line 59 of the coil, the overall characteristics of to guidewire are

Should read:

of the coil, the overall "tortional" characteristics of the guidewire are

Column 6 Line 54 proximal and distal ends the proximal end of said helical

Should read:

proximal and distal ends, the proximal end of said helical

Column 8 Line 14 distal portion of the flexible tubing and the remaining

Should read:

distal portion of the flexible tubing and the retaining

Signed and Sealed this

Tenth Day of March, 2009

JOHN DOLL
*Acting Director of the United States Patent and Trademark Office*